United States Patent [19]

Ando et al.

[11] Patent Number: 5,080,767

[45] Date of Patent: Jan. 14, 1992

[54] PROCESS FOR PREPARING AROMATIC COMPOUNDS HAVING CHLORINATED SIDE CHAINS AND METHOD FOR STABILIZING MONOCHLORO-SIDE CHAIN AROMATIC COMPOUNDS

[75] Inventors: Sinji Ando; Yukio Fukui; Kouji Matui; Takayoshi Masuda, all of Aichi, Japan

[73] Assignee: Mitsui Toatsu Chemicals, Inc., Tokyo, Japan

[21] Appl. No.: 503,967

[22] Filed: Apr. 4, 1990

[30] Foreign Application Priority Data

Apr. 7, 1989 [JP] Japan .................................. 1-87012
Apr. 7, 1989 [JP] Japan .................................. 1-87013

[51] Int. Cl.⁵ .................... C07C 17/42; C07C 17/24; C07C 22/04
[52] U.S. Cl. .................... 204/158.1; 570/111
[58] Field of Search .................... 570/111; 204/158.1

[56] References Cited

U.S. PATENT DOCUMENTS

| | | |
|---|---|---|
| 2,493,427 | 1/1950 | Thomas ........................ 570/111 |
| 2,844,635 | 7/1958 | Mayor ........................ 260/651 |
| 2,998,459 | 8/1961 | Baker et al. .................. 204/158.1 |
| 3,259,561 | 7/1966 | Sievers ........................ 204/158.1 |
| 3,424,805 | 1/1969 | Fruhwirth et al. ............. 260/652.5 |

FOREIGN PATENT DOCUMENTS

| | | | |
|---|---|---|---|
| 1275531 | 4/1969 | Fed. Rep. of Germany . | |
| 44621 | 4/1979 | Japan ........................ | 204/158.1 |
| 48009 | 9/1980 | Japan ........................ | 204/158.1 |
| 154134 | 9/1982 | Japan ........................ | 204/158.1 |

OTHER PUBLICATIONS

"Patent Abstracts of Japan" vol. 8, No. 162 (C-235) (1599) Jul. 26, 1984 Kokai No. 59-65046.
"Patent Abstracts of Japan" (C-78) (2154) Kokai No. 53-77022.

*Primary Examiner*—J. E. Evans
*Attorney, Agent, or Firm*—Burns, Doane, Swecker & Mathis

[57] ABSTRACT

Photochlorination of aromatic compounds having at least one alkyl side chain is carried out in the presence of an alkylene polyamine previously mixed with an aromatic compound having at least one chlorinated side chain whereby side reactions are suppressed.

Aromatic compounds having a monochlorinated side chain are stabilized with an alkylene polyamine. Stainless steel apparatuses can be used in both cases.

8 Claims, No Drawings

PROCESS FOR PREPARING AROMATIC COMPOUNDS HAVING CHLORINATED SIDE CHAINS AND METHOD FOR STABILIZING MONOCHLORO-SIDE CHAIN AROMATIC COMPOUNDS

BACKGROUND OF THE INVENTION

1. Field of the Invention

The invention relates to a process for preparing aromatic compounds having at least one chlorinated side chain by photochlorination of an aromatic compound having at least one alkyl group as a side chain and a method for stabilizing aromatic compounds having at least one chlorinated side chain.

Since aromatic compounds having a chlorinated alkyl side chain or chains, which may be produced by photochlorinating aromatic compounds having an alkyl side chain or chains, have a reactive chlorine atom at the side chain, said compounds are useful as intermediate materials. For example, α- monochloroxylene or α,α'-dichloroxylene, which may be produced by the photochlorination of xylene, can be easily converted to diglycols as raw materials for synthetic resins, diamines as raw materials for nylons and the like. Benzyl chloride, which may be prepared by photochlorinating toluene, can be used as an intermediate for the preparation of benzyl alcohol and the like.

2. Description of the Prior Art

When stainless steel materials are used for reactors in the photochlorination reaction of aromatic compounds having alkyl side chains, iron chloride and the like are formed in the reaction system and cause the production of a lot of nuclear substituted chlorinated products and resinous materials as by-products resulting in a remarkable decrease in yield of the end products, i.e. side chain chlorinated products.

Therefore, heretofore stainless steel materials have not been used, and reactors made of non metallic materials such as glass lined reactors and the like have been used for photochlorinating reactions. In general, the equipment cost of non-metallic materials are so expensive as compared with stainless steel materials that such non-metallic material reactors are not commercially advantageous.

For purposes of solving the problems, various methods have been proposed. For example, it is proposed to use additives such as triallyl phosphates, acetamide, urea, alkyl substituted amides, but these do not give a satisfactory result. U.S. Pat. No. 2,844,635 discloses a halogenating method comprising adding 0.1-10% by weight of alkylene polyamines, but according to the result of the present inventors' investigation, when such a large amount of alkylene polyamines as mentioned in said U.S. Patent is used in a reactor having a stainless steel material, the reaction liquid becomes less transparent and light reaches the inside of the system with difficulty so that, on the contrary, nuclear substituted products are produced in a large amount as by-products, and moreover, stainless steel materials are corroded at a temperature of 120° C. or higher.

In addition, alkylene polyamines easily produce addition products by the reaction with hydrogen chloride as a by-product in the chlorinating reaction The resulting addition products can not effectively suppress the side reactions and therefore this is not a useful method. In view of the foregoing, there is not an effective countermeasure to the drawbacks in the photochlorinating reaction of aromatic compounds having an alkyl side chain or chains. Further, when for example, α-monochloroxylene. benzyl chloride or the like, which may be produced by photochlorinating reactions as above, are allowed to stand, the compounds deteriorate to generate hydrochloric acid and change to resinous materials. The phenomena are particularly remarkable when the temperature is high or metals such as iron, zinc and the like are present, and adversely affect production, purification and storage of α-monochloroxylene. For the purposes of solving the problems, methods for the stabilization by adding amines have been researched. For example, Japanese Patent Laid Open No. 66575/1973 discloses a method of distilling chlorinated xylene or toluene in the presence of an amine such as triethylamine, methyl diethylamine, tripropylamine, tributylamine, aniline, mono- and dialkylaniline, benzylamine, 2,2-dipyridine and the like, alkaline metal salts of aminocarboxylic acids, alkaline metal salts of hydroxycarboxylic acids or alkaline metal salts of condensed phosphoric acids, but these compounds do not give a satisfactory effect.

In addition, in order to solve such problems, Japanese Patent Laid Open Nos. 250329/1988 and 250330/1988 disclose a method of adding stabilizers mainly composed of hexamine. Though hexamine exhibits an excellent stabilizing effect, it was found that hexamine accelerates the corrosion of stainless steel apparatuses or machines when it is kept at an elevated temperature for a long period of time together with α-monochloroxylene or reaction products of chlorination of xylene containing α-monochloroxylene in stainless steel apparatuses or machines.

As mentioned above, at present there is not a method of stabilizing effectively, for example, α-monochloroxylene, benzyl chloride or the like, which may be produced by the photochlorination of aromatic compounds having an alkyl group as a side chain.

SUMMARY OF THE INVENTION

It is an object of the present invention to provide a process for photochlorinating at least one alkyl group as the side chain of aromatic compounds, wherein side reactions are suppressed.

It is another object of the present invention to provide a process for photochlorinating at least one alkyl group as the side chain of aromatic compounds in a reactor having a stainless steel material, wherein side reactions are suppressed.

It is a further object of the present invention to provide a process for photochlorinating at least one alkyl group as the side chain of aromatic compounds in e reactor having a stainless steel material, wherein side reactions are suppressed with a small amount of alkylene polyamine.

It is still another object of the present invention to provide a method of stabilizing aromatic compounds having a monochlorinated side chain or compositions containing said aromatic compounds.

It is still further object of the present invention to provide a method of stabilizing aromatic compounds having a monochlorinated side chain or compositions containing said aromatic compounds in stainless steel material apparatuses or machines.

It is still another object of the present invention to provide a method of stabilizing aromatic compounds having a monochlorinated side chain or compositions containing said aromatic compounds in stainless steel material apparatuses or machines without corroding the stainless steel materials for a long time and/or at a high temperature.

It is still further object of the present invention to provide a method of stabilizing aromatic compounds having a monochlorinated side chain or compositions containing said aromatic compounds by means of an alkylene polyamine at a low cost.

According to one aspect of the present invention, there is provided a process for producing an aromatic compound having at least one chlorinated alkyl group as a side chain which comprises chlorinating an aromatic compound having at least one alkyl group as a side chain with gaseous chlorine in a reactor having at least a stainless steel material in a liquid phase in the presence of light, an alkylene polyamine previously mixed with an aromatic compound having at least one chlorinated side chain being added to the reaction system in an amount of from 0.005 to 1.0% by weight based on the weight of the aromatic compound having at least one alkyl group as a side chain.

According to another aspect of the present invention, there is provided a method of stabilizing an aromatic compound having a monochlorinated side chain or a composition containing said aromatic compound which comprises adding an alkylene polyamine as a stabilizer to said aromatic compound or said composition in an amount of from 0.001 to 1.0% by weight based on said aromatic compound or said composition.

DESCRIPTION OF THE PREFERRED EMBODIMENTS

A feature of the present invention is that the above objects of the present invention can be attained not only when apparatuses such as reactors, towers, vessels and the like made of non-metallic materials, such as glass lining material and the like are used, but also when apparatuses or machines made of stainless steel materials are employed.

Exemplary suitable stainless steel materials include martensite stainless steels such as SUS 403, SUS 410, SUS 414, SUS 416, SUS 420, SUS 431, SUS 440 and the like, ferrite stainless steels such as SUS 430, SUS 446, SUS 405 and the like, and austenite stainless steels such as SUS 301, SUS 302, SUS 303, SUS 304, SUS 305, SUS 308, SUS 321, SUS 347, SUS 304L, SUS 316, SUS 317, SUS 316L, SUS 309, SUS 314 and the like.

According to the present invention, even when a reactor having such stainless steel materials as above is used, the formation of aromatic nuclear substituted products can be suppressed and the side chain chlorinated products can be produced in a high yield.

In addition, even when towers and vessels made of stainless steel materials are used for post-treatments such as distillation, purification and the like and storage of aromatic compounds having a monochlorinated side chain, for example, unstable α-monochloroxylene, the aromatic compounds are not deteriorated, hydrochloric acid is not generated and the apparatuses and machines are not corroded.

Exemplary suitable aromatic compounds having at least one alkyl group as a side chain include aromatic compounds having 1-4 methyl groups attached to a benxene nucleus, for example, toluene, o-xylene, m-xylene, p-xylene, mesitylene including the isomers, durene including the isomers, ethylbenzene, cumene and the like.

The alkylene polyamine may be a compound of the formula,

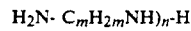

where m is an integer of 2 to 5, and n is an integer of 1 to 10.

Exemplary suitable alkylene polyamines include ethylene diamine, diethylene triamine, triethylene tetramine, tetraethylene pentamine, and pentaethylene hexamine.

The amount of an alkylene polyamine used as a side reaction suppressing agent for the photochlorinating reaction is 0.005-1.0% by weight, preferably 0.005-0.09% by weight, more preferably 0.008-0.09% based on the weight of the aromatic compound having at least one alkyl group as a side chain. The amount of alkylene polyamine to be used is in terms of weight percentage based on the weight of said aromatic compound charged as a starting material in the case of a batch or semi batch system, and is in terms of weight percentage based on the weight of said aromatic compound continuously fed to the reactor in the case of continuous reaction system.

When the amount exceeds the upper limit as mentioned above the reaction mixture becomes less transparent and thereby it is difficult to ensure that light reaches the inside of the reaction system. Therefore, a significant amount of nuclear substituted products are formed as by-products contrary to the goal of the present invention. When the amount is less than the lower limit, a significant amount of nuclear substituted chlorinated products and resinous materials are disadvantageously formed as by-products.

When alkylene polyamine is used as a side reaction suppressing agent for the photochlorinating reaction, it is previously mixed with an aromatic compound having at least one chlorinated side chain, preferably in an amount of 5 times or more the molar amount of the alkylene polyamine.

Exemplary suitable aromatic compounds having at least one chlorinated side chain include benzyl chloride, benzal chloride, benzotrichloride, α-monochloroxylene, α,α-dichloroxylene, α,α'-dichloroxylene and α,α-,α'-trichloroxylene.

Further suitable examples are chloromethyl dimethyl benzene, chloromethyl trimethyl benzene, α-monochloroethyl benzene, α-monochlorocumene, and higher chlorinated products thereof. These chloro-compounds may be produced by chlorinating side chains of mesitylene, durene, ethylbenzene and cumene.

The amount of the aromatic compound having at least one chlorinated side chain to be mixed with the alkylene polyamine is preferably 5 times or more the molar amount of the alkylene polyamine. An amount of less than 5 times is not preferable since the alkylene polyamine can not sufficiently suppress the side reaction in the photochlorinating reaction. The suppressing effect does not further even when said aromatic compound is used in a large amount exceeding the necessary amount.

It is not always necessary that the aromatic compound having at least one chlorinated side chain is a single and pure compound, but it may be used in the form of a mixture of said aromatic compounds. Furthermore, said aromatic compound or compounds may be in the form of a mixture with a starting material, i.e. an aromatic compound having an alkyl side chain or chains such as toluene, xylene, mesitylene and the like and/or nuclear chlorinated aromatic compounds having a chlorinated side chain or chains.

Further, there may be used distillates of a batch or continuous distillation of chlorination products from side chain aromatic compounds. For example, when xylene is chlorinated to produce α,α'-dichloroxylene, α-monochloroxylene is recovered and used again as a starting material so as to enhance the yield. In this case, it is effective to add previously an alkylene polyamine to the α-monochloroxylene.

When benzyl chloride is produced from toluene, it is effective that an alkylene polyamine is incorporated with a part of the benzyl chloride produced in the previous reaction and then the resulting mixture is added to the reaction mixture. When an alkylene polyamine is added without such a treatment as above, a part of the alkylene polyamine forms an addition product with hydrogen chloride as a by-product formed in the chlorinating reaction and thereby the side reaction suppressing effect becomes disadvantageously insufficient.

According to the present invention, the light used for photochlorination is a light containing ultraviolet light. The term "light" is a general term for light containing ultraviolet light generated from a light source usually used in the art such as natural light, mercury lamp, hydrogen discharge tube, flash discharge lamp and the like.

In general, the chlorinating reaction of aromatic compounds having alkyl group as a side chain can be carried out in the presence or absence of a solvent. In the present invention, there are also two cases, that is, a solvent is necessary, depending on the conditions. For example, when an aromatic compound containing alkyl side chains is a solved, it is desirable to dissolve it in a solvent and carry out the chlorination in a liquid phase depending on the reaction conditions.

Exemplary suitable solvents include carbon tetrachloride, chloroform, hexachloroethane, tetrachloroethane and the like.

The reaction temperature may be optionally selected, for example, a temperature not exceeding the boiling point of the aromatic compound containing an alkyl side chain or chains, or when a solvent is used, a temperature not exceeding the boiling point of the solvent. In the chlorination of p-xylene, it is preferable to effect the chlorination at a temperature where the capitalization does not occur since crystals are liable to form at a low temperature.

Chlorine may be fed alone or in combination with an inert gas such as nitrogen and the like.

As mentioned above, according to the present invention, even a small amount of alkylene polyamine can exhibit a sufficient effect as a side reaction (nuclear chlorination) suppressing agent since the alkylene polyamine is incorporated with the reaction system after previously mixing it with en aromatic compound containing a chlorinated side chain or chains.

Alkylene polyamines inherently corrode stainless steel materials in the presence of aromatic compounds having a chlorinated side chain or chains, but according to the present invention, there is not a problem of corrosion because of the small amount of alkylene polyamine used.

According to another aspect of the present invention, aromatic compounds having a monochlorinated side chain or a composition containing said aromatic compounds can be stabilized by means of an alkylene polyamine, that is, degradation of said aromatic compounds can be inhibited and even when said aromatic compounds are held in stainless steel apparatuses and machines such as towers, vessels or the like: for a long period of time at a high temperature, corrosion of such structures is not accelerated.

Exemplary suitable stainless steel materials include those as mentioned above.

An aromatic compound having a monochlorinated side chain or a composition containing said aromatic compound is, for example, an aromatic compound having a monochloroalkyl group as a side chain or a composition containing said compound.

Exemplary suitable monochloroalkyl aromatic compounds or compositions containing said aromatic compounds include benzyl chloride, α-monochloroxylene, chloromethyl dimethyl benzene, chloromethyl trimethyl benzene, α-monochloroethyl benzene, and α-monochlorocumene, or compositions containing the above mentioned monochloroalkyl compound such as reaction products of the chlorination of alkyl side chain aromatic compounds, distillates thereof and the like.

Further examples concerning products of chlorination of toluene or xylene are as shown below.

α-Monochloroxylene includes α-monochloro-p-xylene, α-monochloro-m-xylene, and α-monochloro-o-xylene. Products of chlorination of xylene which contain α-monochloroxylene may be a mixture of α-monochloroxylene; α,α-dichloroxylene, α,α'-dichloroxylene, or α,α,α'-trichloroxylene which is produced by chlorinating p-xylene, m-xylene or o-xylene; higher chlorinated side chain(s)-containing products produced by further chlorination of xylene; xylene; and nuclear chlorinated xylene or both nuclear and side chain chlorinated xylene; or distillates obtained by distilling the mixture batchwise or continuously.

Chlorination products of toluene containing benzyl chloride may be mixtures of benzyl chloride, benzal chloride and benzotrichloride produced by chlorinating the methyl side chain of toluene, toluene, and nuclear chlorinated products produced by direct nuclear chlorination of toluene or the side chain chlorinated products, or distillates collected by a batch or continuous distillation of said mixtures.

When such aromatic compounds having a monochlorinated side chain or the compositions containing said aromatic compounds are subjected to a post-treatment such as distillation and the like, the said aromatic compounds or compositions are exposed to a high temperature for a long time and thereby said compounds or compositions generate hydrochloric acid and are degraded. When these are stored and allowed to stand at room temperature for a long time, the same phenomena are also liable to occur.

The alkylene polyamine is effective in preventing the degradation phenomena. That is, the suppression of degradation can be attained by adding an alkylene polyamine to the aromatic compound having a monochlorinated side chain or a composition containing said aromatic compounds.

The amount of alkylene polyamine is 0.001–1.0% by weight, preferably 0.005–0.1% by weight based on the weight of the aromatic compound having a monochlorinated side chain or a composition containing said aromatic compound. The amount to be added varies depending upon the conditions to which said aromatic compound or said composition is exposed.

When the amount exceeds the upper limit, the stabilizing effect is not further improved and moreover, the corrosion of stainless steel materials is disadvantageously accelerated.

When the amount is less than the lower limit, the desirable effect can not be sufficiently attained.

Alkylene polyamines may be added which are diluted with a solvent such as toluene, xylene, mesitylene, durene, ethylbenzene, cumene and the like and then added to the aromatic compounds having a chlorinated side chain or chains or a composition thereof batchwise or continuously. Needless to say, alkylene polyamine may be added directly without dilution. A sufficiently large effect is exhibited with or without stirring.

The temperature at which alkylene polyamine is added is usually a temperature not exceeding the boiling point of the alkylene polyamine and a temperature not lower than the melting point of the aromatic compound having a monochlorinated side chain or a composition containing said aromatic compound.

The pressure is usually atmospheric pressure, but the effect of alkylene polyamine at reduced or elevated pressure is the same as that at atmospheric pressure.

The reason for the surprising effect of alkylene polyamines in the photochlorination and the stabilization of aromatic compounds having a monochloroalkyl side chain is not clearly understood. Although it is not desired to limit the invention to any particular theory, the mechanism is believed as described below.

Using triethylene tetramine (here referred to as TETA) and $\alpha$-chloroxylene (here referred to as $\alpha$) as an example, when TETA is previously mixed with $\alpha$, a TETA·$\alpha$ salt is formed and this salt is reacted with $FeCl_3$ to form a metal chelate which blocks the catalytic function of metals and thereby the nuclear substitution reaction and the polymerization reaction of aromatic compounds having at least one chlorinated alkyl group as a side chain are inhibited.

On the contrary, when TETA is added without the pretreatment, e.g. previously mixing with an aromatic compound having at least one chlorinated side chain, TETA reacts with hydrochloric acid to form a TETA·HCl salt. Since the TETA·HCl salt does not form a metal chelate as mentioned above, this salt can not block the catalytic function of metals and therefore, when the amount of TETA added is small, a satisfactory result can not be obtained.

In other words, it is believed that an alkylene polyamine and an aromatic compound having at least one chlorinated side chain form an addition product, which reacts with by-products in the photochlorinating reaction system such as metal ions, metal salts and the like and thereby blocks the Lewis acid catalytic function of the metal ion and the like resulting in suppression of the nuclear substitution and polymerization of aromatic compounds having at least one chlorinated alkyl group as a side chain.

According to the present invention, even a small amount of an alkylene polyamine can actually give a large effect. This fact appears to be due to the formation of such salt of an alkylene polyamine and an aromatic compound having at least one chlorinated side chain Since only a small amount of alkylene polyamine is necessary, the reaction mixture does not become less transparent and the apparatuses are not corroded even at a high temperature in the distillation operation.

As mentioned above, the present invention has various advantages. In the photochlorinating reaction, the side reaction such as the formation of nuclear chlorinated products, resinous materials and the like can be suppressed to mainly produce aromatic compounds having at least one chlorinated alkyl group as a side chain; the reaction can be effectively carried out in stainless steel apparatuses which is relatively inexpensive as compared with non-metallic material apparatuses: and further a small amount of alkylene polyamine is enough.

In addition, aromatic compounds having a monochlorinated side chain or compositions containing said aromatic compounds can be stabilized, for example, degradation of said compounds can be inhibited, and when stainless steel apparatuses or machines are used for treating or handling said aromatic compounds even at a high temperature and/or for a long period of time, corrosion of the stainless steel materials are not accelerated. Furthermore. alkylene polyamines as the stabilizer are inexpensive.

The following examples are presented to illustrate the present invention. The following comparative examples and reference examples are given to help to understand the present invention.

EXAMPLE 1

To 100 g. of a solution composed of 50% by weight of $\alpha$-monochloro-p-xylene and 50% by weight of p-xylene, was added 10 g. of triethylene tetramine, to prepare a triethylene tetramine containing solution.

500 g. of p-xylene was added to a 1 liter reactor made of SUS 304 and equipped with a jacket, a reflux condenser, a stirrer, a chlorine gas inlet pipe and an internal 100 W high pressure lamp for irradiation.

Then, 0.5 g. of the above-mentioned triethylene tetramine-containing solution was added to the p-xylene such that triethylene tetramine amounted to 0.01% by weight based on the p-xylene. The reaction temperature was kept at 75° C. by passing warm water through the jacket and chlorine gas was blown through the reaction mixture at a velocity of 10 g./min. with stirring to carry out a chlorinating reaction. The amount of chlorine blown through was 400 g. in total. Chlorine was not substantially detected in the exhaust gas from the reactor, various chlorinated products in the reaction mixture were analyzed by gas chromatography. As a result, nuclear substituted products and resinous products were only 1.9%. A detailed analysis is shown in Table 1.

EXAMPLE 2-8, 11, 12 AND COMPARATIVE EXAMPLES 1-3

The procedure in Example 1 was repeated under the conditions as shown in Table I to carry out the photo chlorinating reaction. The results are shown in Table 1.

EXAMPLE 9

To 100 g. of a solution of benzyl chloride 10% by weight and toluene 90% by weight was added 1 g. of triethylene tetramine.

The triethylene tetramine-containing solution (10 g.) thus separately prepared was added to 500 g. of toluene in the same reactor set forth in Example 1 such that the amount of triethylene tetramine was 0.02% by weight based on the weight of the toluene.

The reaction temperature was kept at 50° C. by passing warm water through the jacket and chlorine gas was blown through the reaction mixture at a rate of 5 g./min. with stirring to carry out the chlorinating reaction, and 420 g. of chlorine gas was blown through in total. Chlorine was scarcely detected in the exhaust gas from the reactor. Analysis of various chlorinated products in the reaction mixture was conducted by gas chromatography. The result showed: toluene 3.0% by weight, benzyl chloride 76% by weight, benzal chloride 20% by weight, benzotrichloride 0.1% by weight, and nuclear substituted products and resinous products 0.9% by weight.

EXAMPLE 10

The same reactor set forth in Example 1 except that it was further equipped with a xylene feeding port at the bottom and a reaction mixture discharging nozzle at a level of 500 ml. volume, was used for a continuous chlorinating reaction.

To a solution containing 35% by weight of p-xylene, 60 % by weight of α-monochloro-p-xylene, 5% by weight of others was added triethylene tetramine such that the amount of triethylene tetramine, was 200 ppm. The reactor was charged with the resulting mixture of the starting materials and then the mixture was continuously fed to the reactor at a rate of 20 g./min. While chlorine was blown through the reaction mixture ar a rate of 9 g./min. The chlorinating reaction was carried out with stirring while keeping the temperature at 70° C. by passing cold water through the jacket. When the volume of the mixture of the starting materials fed to the reactor became 5 times the volume of the reactor, the reaction mixture was sampled and analysis of the chlorinated products therein was conducted by gas chromatography.

As a result, it was found that the mixture contained p-xylene 12% by weight, α-monochloro-p-xylene 56.5% by weight, α,α-dichloro-p-xylene 5.1% by weight, α,α'-dichloro-p-xylene 20.5% by weight, α,α,α'-trichloro-p-xylene 3.8% by weight, nuclear substituted products and resinous products 2.1% by weight. Chlorine was scarcely detected in the exhaust gas from the reactor.

REFERENCE EXAMPLE 1

In a 100 ml. glass flask were placed 50 ml. of the reaction mixture in Example 1 and a test piece (surface area 20.253 cm², weight 24.412 g) of a flat plate SUS 304, and warmed at 130° C. for 24 hours. After taking out the test piece from the flask, it was simply washed with water, then with acetone, dried and the decrease in its weight was measured to determine the degree of corrosion (mm/year). As a result, the degree of corrosion was 0.

The degree of corrosion (mm/year) was calculated by the following formula, $$\text{Degree of Corrosion} = [((W_i - W_f) \times 365)/(S \times d \times \text{day})] \times 10$$

$W_i$ = Weight of a test piece before immersion (g)
$W_f$ = Weight of the test piece after immersion (g)
$S$ = Surface area of the test piece (cm²)
$d$ = Specific gravity of the test piece

REFERENCE EXAMPLE 2

The same procedure set forth in Reference Example 1 was repeated except that 50 ml of the reaction mixture of Comparative Example 2 was used and a test piece of a flat plate of SUS 304 (surface area 20.253 cm², weight 24.412 g.) was immersed therein and kept at 130° C. for 24 hours. The degree of corrosion was 1.28 (C grade anticorrosion) so that the test piece material was found to be unusable.

TABLE 1

| | Conditions | | | | | | | | |
|---|---|---|---|---|---|---|---|---|---|
| | | | | Alkylene polyamine | | | | Chlorine | |
| | Starting material | | | Type of aromatic compound having chlorinated side chain | Type of alkylene polyamine | Wt. | | Amount blown through | Blowing rate |
| | Compound | g. | Mole | (*1) | | g. | % | g. Mole | g./min. |
| Example No. | | | | | | | | | |
| 1 | p-Xylene | 500 | 4.71 | A | Triethylene tetramine | 0.05 | 0.01 | 400 5.64 | 10 |
| 2 | " | " | " | " | Triethylene tetramine | 0.25 | 0.05 | " " | " |
| 3 | " | " | " | B | Triethylene tetramine | 0.05 | 0.01 | " " | " |
| 4 | " | " | " | A | Diethylene triamine | " | " | " " | " |
| 5 | " | " | " | " | Tetraethylene pentamine | " | " | " " | " |
| 6 | " | 100 | 0.94 | " | Triethylene tetramine | 0.01 | " | 80 1.13 | " |
| 7 | " | 500 | 4.71 | " | Triethylene tetramine | 0.05 | " | 400 5.64 | " |
| 8 | m-Xylene | " | " | C | Triethylene tetramine | " | " | " " | " |
| 11 | p-Xylene | " | " | A | Pentaethylene hexamine | " | " | " " | " |
| 12 | " | " | " | " | Triethylene tetramine | 4.50 | 0.9 | " " | " |
| Comparative Example No. | | | | | | | | | |
| 1 | p-Xylene | " | " | none | Triethylene tetramine | " | " | " " | " |
| 2 | " | " | " | " | Triethylene tetramine | 10 | 2 | " " | " |
| 3 | " | " | " | A | Triethylene | 0.01 | 0.002 | " " | " |

TABLE 1-continued

| | Conditions | | | | tetramine Result (*2) | | | | | | |
|---|---|---|---|---|---|---|---|---|---|---|---|
| | Solvent | | Temperature | Apparatus | | | | α | αα | Nuclear substituted products and resinous | |
| | Type | g. | °C. | material | Xylene | α | αα | α' | α' | products | Remarks |
| Example No. | | | | | | | | | | | |
| 1 | none | — | 75 | SUS 304 | 7.0 | 53.9 | 7.0 | 27.5 | 2.7 | 1.9 | |
| 2 | " | — | " | SUS 316 | 7.0 | 54.2 | 7.0 | 27.6 | 2.6 | 1.6 | |
| 3 | " | — | " | SUS 304 | 6.9 | 54.0 | 7.0 | 27.6 | 2.5 | 2.0 | |
| 4 | " | — | " | " | 6.9 | 54.2 | 6.9 | 27.5 | 2.8 | 1.7 | |
| 5 | " | — | " | " | 7.1 | 54.4 | 6.9 | 27.3 | 2.6 | 1.7 | |
| 6 | Carbon tetrachloride | 500 | 50 | SUS 304L | 7.0 | 54.3 | 6.8 | 27.6 | 2.5 | 1.8 | Carbon tetrachloride is excluded in the analytical values |
| 7 | none | — | 75 | SUS 430 | 6.9 | 54.2 | 6.9 | 27.1 | 2.6 | 2.3 | |
| 8 | " | — | 50 | SUS 304 | 6.8 | 53.6 | 7.0 | 27.2 | 2.5 | 2.9 | |
| 11 | " | — | 75 | " | 7.0 | 54.1 | 6.9 | 27.4 | 2.7 | 1.9 | |
| 12 | " | — | 75 | " | 6.9 | 53.9 | 6.7 | 27.1 | 2.5 | 2.9 | |
| Comparative Example No. | | | | | | | | | | | |
| 1 | " | — | 75 | " | 8.5 | 51.0 | 5.5 | 24.8 | 1.8 | 8.4 | Much unreacted chlorine |
| 2 | " | — | " | " | 6.9 | 53.5 | 6.7 | 26.3 | 2.5 | 4.1 | Less transparent reaction liquid |
| 3 | " | — | " | " | 14.0 | 49.0 | 4.0 | 16.0 | 1.3 | 15.7 | Much unreacted chlorine |

*1 A: α-Monochloro-p-xylene 50 wt. %, p-xylene 50 wt. %.
B: α-Monochloro-p-xylene 5 wt. %, p-xylene 90 wt. %, others 5 wt. %. 0.5 g. of triethylene tetramine was added to 100 g. of this B solution.
C: α-Monochloro-m-xylene 50 wt. %, m-xylene 50 wt. %.
*2 α: α-Monochloroxylene
αα: α,α-Dichloroxylene
αα': α,α'-Dichloroxylene
ααα': α,α,α'-Trichloroxylene
The numerals in "Result" are % by weight.

EXAMPLE 13

A triethylene tetramine containing solution was previously prepared by mixing 100 g. of a solution of 50% by weight of 1-chloromethyl-3,5-dimethyl benzene and 50% by weight of mesitylene and 10 g. of triethylene tetramine and charged in the same reactor set forth in Example 1 containing 500 g. Of mesitylene in an amount of 0.5 g. such that the amount of triethylene tetramine was 0.01% by weight based on the weight of mesitylene.

In the same manner set forth in Example 1, chlorine was blown through the reaction starting material mixture to carry out a chlorinating reaction and 295 g. of chlorine was used in total. Chlorine was not substantially found in the exhaust gas from the reactor.

The reaction mixture after the chlorination was analyzed by gas chromatography. It was found that 54% of 1-chloromethyl-3,5-dimethylbenzene and as little as 4.3% of nuclear substituted products and resinous products were obtained.

EXAMPLE 14

To a 100 ml. of glass flask were added p-xylene 50 g., ferric chloride 50 ppm, and diethylene triamine 0.01% by weight, kept at 100° C. for 48 hours and the hydrochloric acid thus produced was quantitatively measured. The amount of the generated hydrochloric acid was $2.4 \times 10^{-5}$ mole/hour and a deterioration of α-monochloro-p-xylene was very little.

EXAMPLES 15-23 and COMPARATIVE EXAMPLES 4-7

In a 100 ml. glass flask was placed 50 g. of a chlorinated product and an additive in Table 2 and kept at a temperature under the condition as shown in Table 2. The amount of the hydrochloric acid thus produced was determined for comparing the stability. The results are shown in Table 2.

EXAMPLES 24-28 AND COMPARATIVE EXAMPLES 8-11

In a 100 ml. glass flask were placed a material test piece (a flat plate), 50 g. of a chlorinated product and an additive as shown in Table 3 and kept ar a temperature under the condition as shown in Table 3. The hydrochloric acid thus produced was quantitatively determined and the corrosion of the material test piece was examined.

For evaluating the corrosion, the test piece as taken out from the flask, simply washed with water and then with acetone, dried and the decrease in its weight was measured to determine the degree of corrosion (mm/year). The calculation was made according to the formula set forth in Reference Example 1. The results are shown in Table 3.

TABLE 2

| Example No. | Chlorinated product | Additive Ferric chloride (ppm) | Stabilizer Compound | Stabilizer Amount (wt. %) | Conditions Temperature °C. | Conditions Time hr. | Amount of generated hydrochloric acid mol./hr. | Remarks |
|---|---|---|---|---|---|---|---|---|
| 14 | α-Monochloro p-xylene | 50 | Diethylene triamine | 0.01 | 100 | 48 | $2.4 \times 10^{-5}$ | |
| 15 | α-Monochloro p-xylene | " | Triethylene tetramine | 0.01 | " | " | $2.5 \times 10^{-5}$ | |
| 16 | α-Monochloro-m-xylene | " | Triethylene tetramine | 0.1 | " | " | $2.0 \times 10^{-5}$ | |
| 17 | α-Monochloro-o-xylene | " | Triethylene tetramine | 0.5 | " | " | $1.0 \times 10^{-5}$ | |
| 18 | α-Monochloro-p-xylene | " | Triethylene tetramine | 0.05 | 200 | " | $5.0 \times 10^{-5}$ | |
| 19 | α-Monochloro-p-xylene | " | Tetraethylene pentamine | 0.05 | " | " | $4.0 \times 10^{-5}$ | |
| 20 | Chlorinated reaction products (*1) | " | Triethylene tetramine | 0.05 | 100 | " | $2.0 \times 10^{-5}$ | |
| 21 | Distillates (*2) | " | Triethylene tetramine | 0.05 | " | " | $2.1 \times 10^{-5}$ | |
| 22 | α-Monochloro p-xylene | 0 | Triethylene tetramine | 0.05 | " | " | $1.0 \times 10^{-5}$ | |
| 23 | Benzyl chloride | 50 | Triethylene tetramine | 0.05 | 100 | " | $1.8 \times 10^{-5}$ | |
| Comparative Example No. | | | | | | | | |
| 4 | α-Monochloro p-xylene | 0 | none | — | 100 | 48 | $1.7 \times 10^{-4}$ | |
| 5 | α-Monochloro p-xylene | 50 | " | — | " | 0.5 | 0.35 | *3 |
| 6 | Benzyl chloride | " | " | — | " | " | 0.34 | *3 |
| 7 | α-Monochloro-p-xhlene | " | Triethylene tetramine | 0.0008 | " | " | 0.15 | *3 |

*1 p-Xylene 11.0%, α-monochloro-p-xylene 58.0%, α,α-dichloro-p-xylene 3.0%, αα'-dichloro-p-xylene 25.0%, α,α,α'-trichloro-p-xylene 1.5%, others 1.5%
*2 p-Xylene 10.0%, α-monochloro-p-xylene 85.0%, α,α-dichloro-p-xylene 3.0%, others 2%
*3 Hydrochloric acid abruptly generates immediately after starting the test.

TABLE 3

| Example No. | Chlorinated product | Stabilizer Compound | Stabilizer Amount (wt. %) | Test piece | Conditions Temperature °C. | Conditions Time (hr.) | Amount of generated hydrochloric acid | Degree of corrosion of test piece | Evaluation | Remarks |
|---|---|---|---|---|---|---|---|---|---|---|
| 24 | α-Monochloro-p-xylene | Triethylene tetramine | 0.05 | SUS 304 | 180 | 48 | $3.0 \times 10^{-5}$ | 0 | Completely corrosion-resistant | |
| 25 | α-Monochloro-p-xylene | Triethylene tetramine | " | SUS 316 | " | " | $2.5 \times 10^{-5}$ | " | Completely corrosion-resistant | |
| 26 | α-Monochloro-p-xylene | Triethylene tetramine | " | SUS 316L | " | " | $2.3 \times 10^{-5}$ | " | Completely corrosion-resistant | |
| 27 | α-Monochloro-p-xylene | Triethylene tetramine | " | SUS 430 | " | " | $3.5 \times 10^{-5}$ | " | Completely corrosion-resistant | |
| 28 | α-Monochloro-p-xylene | Triethylene tetramine | " | SUS 403 | " | " | $3.4 \times 10^{-5}$ | " | Completely corrosion-resistant | |
| Comparative Example No. | | | | | | | | | | |
| 8 | α-Monochloro-p-xylene | none | — | SUS 304 | 180 | 0.5 | 0.30 | 1.5 | C-grade | *1 |
| 9 | α-Monochloro-p-xylene | " | — | SUS 316 | " | " | 0.28 | 1.3 | C-grade | *1 |
| 10 | α-Monochloro-p-xylene | Hexamine | 0.05 | SUS 304 | " | 48 | $7.8 \times 10^{-5}$ | 0.15 | B-grade | |
| 11 | α-Monochloro- | " | " | SUS 316 | " | " | $7.3 \times 10^{-5}$ | 0.10 | A-grade | |

TABLE 3-continued

| Chlorinated product | Stabilizer Compound | Amount (wt. %) | Test piece | Conditions Temperature °C. | Time (hr.) | Amount of generated hydrochloric acid | Degree of corrosion of test piece | Evaluation | Remarks |
|---|---|---|---|---|---|---|---|---|---|
| p-xylene | | | | | | | | | |

*1 Hydrochloric acid abruptly generates immediately after starting the test.

EXAMPLE 29

Triethylene tetramine (0.05 g.) was added to 500 g. of the reaction mixture in Example 1 taken out after chlorination and the resulting mixture was used as a raw material for distillation. The raw material was placed in a container made of SUS 304 and subjected to a batch distillation by means of a 10-plate distillation apparatus of OLDERSHAW type (made of glass, a plate tower type).

At a reflux ratio of 20 and 20 mmHg of a tower top vacuum, a distillate fraction 1 up to 95° C. of the tower top temperature, a distillate fraction 2 up to 120° C. and a distillate fraction 3 up to 135° C. were collected and subjected to a gas chromatography to analyze the compositions of fractions 1-3 and the bottom residue. The results are shown in Table 4.

Since fraction 1 is composed of unreacted p-xylene and α-monochloro-p-xylene, it can be used again for the reaction. In fraction 3, the α,α'-dichloro p-xylene was of a purity of 98.3%.

During the distillation, α-monochloro-p-xylene was scarcely converted to a resinous material and only a small amount of hydrochloric acid was generated.

TABLE 4

| | Weight (g.) | Composition (wt. %) | | | | | |
|---|---|---|---|---|---|---|---|
| | | p-Xylene | α-Monochloro-p-xylene | α,α-Dichloro-p-xylene | α,α'-dichloro-p-xylene | α,α,α'-Trichloro-p-xylene | Others |
| Fraction 1 | 298.5 | 11.7 | 88.3 | 0 | 0 | 0 | 0 |
| Fraction 2 | 46.4 | 0 | 8.6 | 74.1 | 15.1 | 0 | 2.2 |
| Fraction 3 | 125.6 | 0 | 0 | 0.5 | 98.3 | 0.8 | 0.4 |
| Bottom residue | 29.0 | 0 | 0 | 0 | 24.1 | 43.1 | 32.8 |

What is claimed is:

1. A process for producing an aromatic compound having at least one chlorinated alkyl group as a side chain which comprises chlorinating an aromatic compound having at least one alkyl group as a side chain with gaseous chlorine in a reactor constructed at least partly of stainless steel material in a liquid phase and in the presence of light and an alkylene polyamine which has been previously mixed with an aromatic compound having at least one chlorinated side chain, said alkylene polyamine being added to the reaction system in an amount of from 0.005 to 1.0% by weight based on the weight of the aromatic compound having at least one alkyl group as a side chain.

2. The process according to claim 1 in which the alkylene polyamine is in an amount of from 0.005 to 0.09% by weight based on the weight of the aromatic compound having at least one alkyl group as a side chain.

3. The process according to claim 1 in which the alkylene polyamine is in an amount of from 0.008 to 0.09% by weight based on the weight of the aromatic compound having at least one alkyl group as a side chain.

4. The process according to claim 1 in which the alkylene polyamine is a compound of the formula, $$H_2N-(C_mH_{2m}NH)_n-H$$

where m is an integer of from 2 to 5 and n is an integer of from 1 to 10.

5. The process according to claim 1 in which the aromatic compound having at least one alkyl group as a side chain is a member selected from the group consisting of aromatic compounds having 1-4 methyl groups attached to the benzene nucleus, ethylbenzene, and cumene.

6. The process according to claim 1 in which the aromatic compound having at least one alkyl group as a side chain is a member selected from the group consisting of toluene, o-xylene, m-xylene, p-xylene, mesitylene, durene, ethylbenzene and cumene.

7. The process according to claim 1 in which the aromatic compound having at least one chlorinated side chain is a member selected from the group consisting of benzyl chloride, benzal chloride, benzotrichloride, α-monochloroxylene, α,α-dichloroxylene, α,α'-dichloroxylene, α,α,α'-trichloroxylene, chloromethyl dimethyl benzene, chloromethyl trimethyl benzene, α-monochloroethylbenzene and α-monochlorocumene.

8. The process according to claim 1 in which the amount of the an aromatic compound having at least one chlorinated side chain used is at least 5 times the molar amount of the alkylene polyamine.

* * * * *